US008657848B2

(12) United States Patent
Jenson et al.

(10) Patent No.: US 8,657,848 B2
(45) Date of Patent: Feb. 25, 2014

(54) MAGNETICALLY RETRIEVABLE VENA CAVA FILTER AND RETRIEVAL DEVICE THEREFOR

(75) Inventors: Mark L. Jenson, Greenfield, MN (US); Roger Hastings, Maple Grove, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 187 days.

(21) Appl. No.: 13/253,480

(22) Filed: Oct. 5, 2011

(65) Prior Publication Data

US 2012/0130418 A1    May 24, 2012

Related U.S. Application Data

(60) Provisional application No. 61/415,109, filed on Nov. 18, 2010.

(51) Int. Cl.
*A61M 29/00* (2006.01)
(52) U.S. Cl.
USPC .......................................... 606/200
(58) Field of Classification Search
USPC .................. 606/200, 213; 335/207
See application file for complete search history.

(56) References Cited

U.S. PATENT DOCUMENTS

| | | | |
|---|---|---|---|
| 4,865,030 A | 9/1989 | Polyak | |
| 6,368,338 B1* | 4/2002 | Konya et al. | 606/200 |
| 6,371,971 B1* | 4/2002 | Tsugita et al. | 606/200 |
| 6,417,750 B1 | 7/2002 | Sohn | |
| 6,551,304 B1 | 4/2003 | Whalen et al. | |
| 6,773,448 B2* | 8/2004 | Kusleika et al. | 606/200 |
| 6,838,963 B2 | 1/2005 | Zimmerling et al. | |
| 7,087,069 B2* | 8/2006 | Petrovic et al. | 606/200 |
| 7,091,806 B2 | 8/2006 | Zimmerling et al. | |
| 7,609,061 B2 | 10/2009 | Hochmair | |
| 7,618,435 B2* | 11/2009 | Opolski | 606/213 |
| 7,799,050 B2* | 9/2010 | Hensley et al. | 606/200 |
| 2009/0157115 A1 | 6/2009 | Fleming | |
| 2010/0004716 A1 | 1/2010 | Zimmerling et al. | |
| 2010/0228281 A1* | 9/2010 | Gilson et al. | 606/200 |

OTHER PUBLICATIONS

"Rare-Earth Magnets" catalog, date unknown, pp. 1-59.
"Low-hysteresis loss ferrite material for Low-THD xDSL modem transformers, DN70 material" website excerpt, date unknown, pp. 1-5.

* cited by examiner

*Primary Examiner* — S. Thomas Hughes
*Assistant Examiner* — Tin Nguyen
(74) *Attorney, Agent, or Firm* — Seager, Tufte & Wickhem LLC

(57) ABSTRACT

The disclosure pertains to magnetically retrievable vena cava filters having a low torque associated therewith when subjected to a strong external magnetic field and retrieval devices therefor. The vena cava filter may include a magnetically permeable sphere or a spherical dipole magnet located within the spherical cavity of the apical hub wherein the spherical dipole magnet is free to rotate about any of three mutually orthogonal axes. The retrieval device is capable of substantially containing the vena cava filter in a collapsed state and includes a magnetically active member capable of interacting with the vena cava filter. The retrieval device may optionally include a supplemental mechanical latch.

4 Claims, 11 Drawing Sheets

MAGNETICALLY RETRIEVABLE VENA CAVA FILTER AND RETRIEVAL DEVICE THEREFOR

RELATED APPLICATIONS

This application claims priority to U.S. Provisional Application Ser. No. 61/415,109 filed Nov. 18, 2010.

BACKGROUND

Magnetic positioning and retrieval devices for implantable medical devices may offer advantages with respect to both ease of alignment and engagement; however the presence of magnetically active elements such implantable devices may result in undesirable effects if the patient subsequently requires or would benefit from exposure to strong external magnetic fields such as those employed for Magnetic Resonance Imaging (MRI). In particular, a magnetic element which is not aligned with the external magnetic field may experience a torque tending to twist the magnetic element and the associated medical device. In addition, the misaligned field may tend to demagnetize the magnetic element thereby rendering it less suited for magnetic retrieval. These effects may exclude the patient from certain important diagnostic measures.

These considerations are particularly important for devices such as, for example vena cava filters which are commonly implanted for extended periods of time. Vena cava filters often are emplaced and never retrieved, remaining effective during their time in place, and remaining permanently in place. However, in some cases it may be desirable to remove or reposition a medical filter after it has been in place for a period of time. Retrieval of medical filters can be challenging. One method of retrieval involves use of a catheter with a loop which is pushed out of the catheter and used to snare a hook on the end of a filter. One of the most difficult aspects of vascular and other medical filter retrievals is locating or aligning the correct part of the filter with the operative end or loop of the retrieval catheter. The surgeon is often working through a long catheter extending through a tortuous anatomy while viewing a shadowy image of the filter and retrieval catheter loop in a two dimensional fluoroscopy image. Fluid flow within the vein or body passage may further increase the challenge.

In light of these challenges, it would be beneficial to have an improved device and method for removal or repositioning of vascular and other medical filters. It would also be desirable to have a practical and economical system and method which facilitate removal of medical filters after implantation. It would be further desirable to have a retrieval system and method which can reduce the time required for retrieval and which can be used even under view of a shadowy, two dimensional image. Furthermore it would be desirable to have a retrieval system and method which can be used from either a femoral or jugular approach and which can be adapted for use with a wide variety of medical filter designs.

Further, it would be beneficial to provide implantable medical devices, such as vena cava or other filters, which are both magnetically retrievable from the body and which avoid the difficulties which may be encountered when magnetic elements are subjected to strong external magnetic fields.

SUMMARY

This disclosure pertains to magnetically retrievable medical devices, such as vena cava filters, wherein such magnetically retrievable medical devices experience a low torque when subjected to a strong magnetic field and to retrieval devices adapted for use therewith.

In some embodiments, the magnetically retrievable vena cava filter comprises an apical hub; a plurality of legs each having a first end fixedly attached to the apical hub and a second free end, said plurality of legs defining a generally conical filter basket in a deployed configuration; a magnetically permeable sphere fixedly attached to the apical hub.

In other embodiments, the magnetically retrievable vena cava filter comprises an apical hub defining therein a generally spherical cavity; a plurality of legs each having a first end fixedly attached to the apical hub and a second free end, said plurality of legs defining a generally conical filter basket in a deployed configuration; and a spherical dipole magnet located within the spherical cavity of the apical hub wherein the spherical dipole magnet is free to rotate about any axis passing through the center of the sphere.

Each of the plurality of legs of the vena cava filters may have a tissue anchor associated with its free end. In other embodiments, the filter may include a first plurality of legs having tissue anchors and a second plurality of legs which are free of tissue anchors.

A retrieval device for a magnetically retrievable vena cava filter may include an elongated shaft having a proximal end and a distal end; a housing having a proximal end, a distal end, and a lumen therebetween wherein the proximal end of the housing is fixedly attached to the distal end of the elongated shaft, said housing being sized and adapted to receive substantially an entire magnetically retrievable vena cava filter in a collapsed configuration; and a magnetically active member actuatable within the housing from a first position in which at least a portion of the magnetically active member extends distally beyond the housing to a second position in which the magnetically active member is located near the proximal end of the housing.

DETAILED DESCRIPTION

Figure 1:
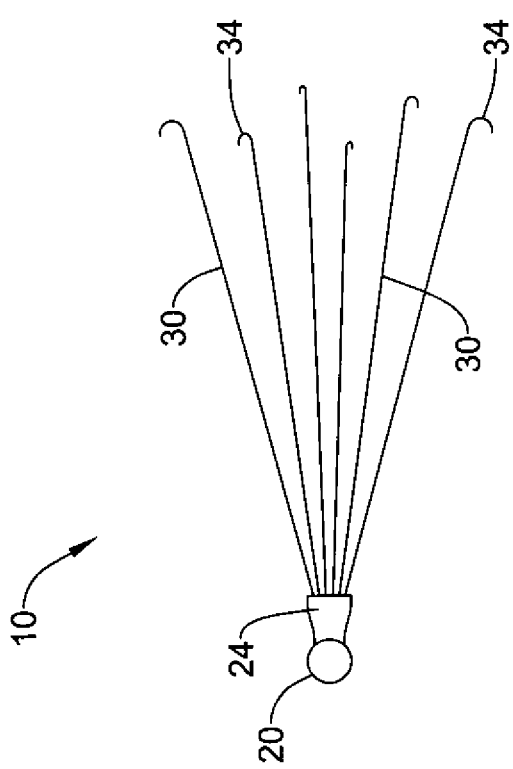
FIG. 1 illustrates a first embodiment of a magnetically retrievable vena cava filter.

The following description should be read with reference to the drawings wherein like reference numerals indicate like elements throughout the several views. The drawings, which are not necessarily to scale, are not intended to limit the scope of the claimed invention. The detailed description and drawings illustrate example embodiments of the claimed invention.

All numbers are herein assumed to be modified by the term "about" The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments whether or not explicitly described in combination.

FIG. 1 illustrates a magnetically retrievable vena cava filter of the present invention shown and generally indicated by the reference numeral 10. The vena cava filter 10 includes a plurality of wire or ribbon legs 30 which have a generally conical deployed state. The plurality of legs 30 may have any of the configurations known in the art including various curved, bent, or bifurcated sections. The legs 30 may be self-deploying, thermally activated, or may employ any of various leg deploying means known in the art. Generally, the plurality of legs 30 will each have a first end joined to an apical head 24 and a second free end configured to engage the wall of a vessel in which it may be deployed. The wall engaging portion of the filter legs 30 may include tissue engaging hooks 34 as illustrated and/or other structures (not shown) such as a positioning stent portion. In addition, the filter may include additional legs (not shown) which serve to center the filter within the vessel.

In one embodiment, attached to the apical head 24 is a solid sphere 20 of magnetically permeable material having low hysteresis. Suitable materials include mu metal, soft iron, nickel-iron alloys commonly known as permalloy, nickel-iron-molybdenum commonly known as supermalloy, iron-silicon-aluminum alloys commonly known as Sendust, iron-boron-silicon alloys commonly known as Metglas® available from Metglas, Inc. (Conway, S.C.) or low-hysteresis loss ferrites such as DN40 and DN70 available from TDK Corp., (Ichikawa, Japan).

Figure 1A:
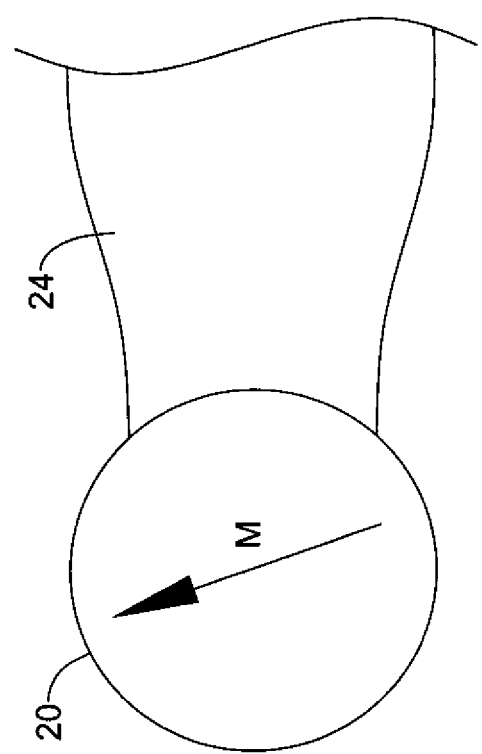
FIG. 1A illustrates the alignment of the magnetization of a magnetically permeable sphere
Figure 1A:
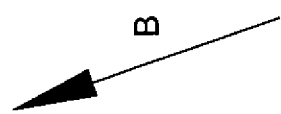

When the magnetically permeable sphere 20 is placed in a strong external magnetic field, such as that found in an MRI apparatus, its magnetization aligns with the external magnetic field direction as shown in FIG. 1A and thus the sphere 20 and associated vena cava filter 10 experience no significant torque as a result of the externally applied field. When a magnet 52, 152 or energized electromagnet 252, associated with a retrieval device to be described below, is positioned near the magnetically permeable sphere 20, it is attracted to the magnet 52, 152, 252 to effect or assist in effecting the retrieval of the vena cava filter 10.

Figure 2:
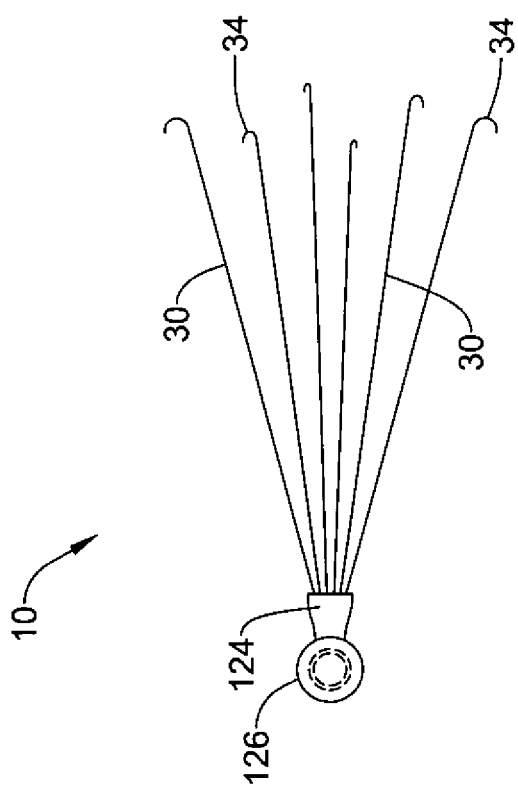
FIG. 2 illustrates another embodiment of a magnetically retrievable vena cava filter.
Figure 2A:
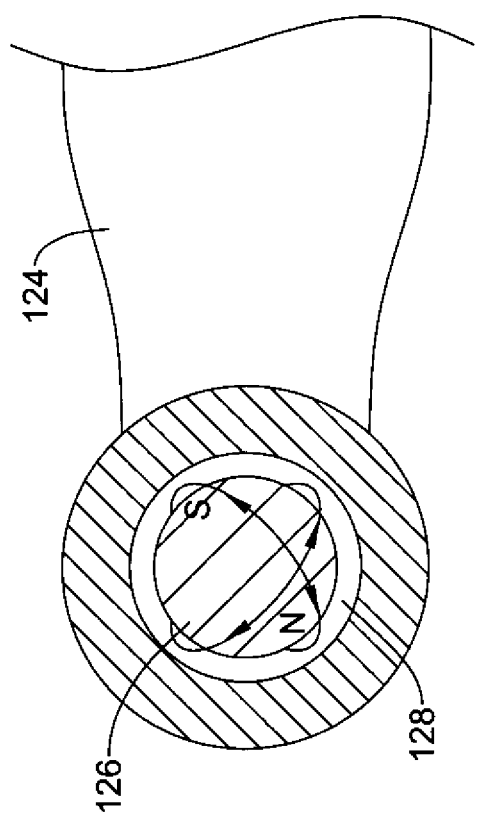
FIG. 2A illustrates a detail of the apical head of the embodiment of FIG. 2.

In an alternate embodiment illustrated in FIG. 2, the sphere 20 of magnetically permeable material and apical head 24 may be replaced by an apical head 124 defining an internal spherical cavity 128 or a cage (not illustrated) containing a spherical dipole magnet 126, said spherical dipole magnet 126 being free to rotate about any axis passing through the center of the sphere. In some embodiments, the spherical dipole magnet 126 may comprise oriented neodymium-iron-boron, samarium-cobalt, or equivalent magnetic materials. In other embodiments, the spherical dipole magnet 126 may include a coating which is capable of reducing friction between the magnet and the walls of the cavity 128 or cage. In yet other embodiments, the spherical dipole magnet 126 may comprise a bar magnet encased in a spherical shell of non-magnetic material.

Although it is desirable to have the spherical dipole magnet 126 nearly fill the cavity 128 or cage in the apical head 124, it is useful to include a small gap between the walls of the cavity 128 and the spherical dipole magnet 126 to ensure that the spherical dipole magnet 126 is able to rotate freely within the cavity 128 or cage. To promote free rotation of the spherical dipole magnet 126 within the cavity 128 or cage, one or both of the spherical dipole magnet 126 and the apical head 124 may be fabricated using a material having a low coefficient of friction such as polyethylene or polytetrafluoroethylene. Such materials may also tend to protect the magnetic material of the spherical dipole magnet from corrosion by bodily fluids. In some embodiments, it may be desirable to include a number of small surface irregularities on one or both of the spherical dipole magnet 126 and the cavity 128 to reduce the contact area therebetween. In other embodiments, it may be desirable to include a lubricating fluid, such as a ferrofluid to occupy the space between the spherical dipole magnet 126 and the cavity 128. In yet other embodiments, bodily fluids may provide a lubricating fluid. In still other embodiments, the spherical dipole magnet 126 may be sealed within the cavity 128. In general, it is desirable that the wall of the apical head be relatively thin or absent in the direction from which a magnetically active material 152 associated with a retrieval device 70 is expected to approach. In addition to the magnet 52 or energized electromagnet 252, associated with a retrieval device for the vena cava filter 10 embodiment of FIG. 1, a magnetically permeable material having low hysteresis, similar to those used to fabricate the magnetically permeable sphere 20, discussed above, may also be satisfactory to effect or assist in effecting the retrieval of the vena cava filter 10 of the embodiment of FIG. 2.

The vena cava filters 10 of FIGS. 1 and 2 are well suited for retrieval and/or repositioning using a device which employs an magnetically active material including a magnet 52, electromagnet 152, or in some cases a magnetically permeable material having low hysteresis to locate and position the retrieval device 70 relative to the apical head 24 and/or magnetically permeable sphere 20. In addition, the magnetically active material associated with the retrieval device 70 may hold the vena cava filter 10 as a retrieval housing is advanced over the vena cava filter 10 and/or as the vena cava filter 10 is withdrawn into the retrieval device. It will be appreciated that the contacting surface of the magnetically active material 52, 152, 252 or an equivalent element fabricated from magnetically permeable material may be shaped to enhance attraction between the magnetically active material and the magnetically permeable sphere 20 or apical head 124. For example, the distal end of the magnetically active material 52 may form a hemispherical cavity which receives the magnetically permeable sphere 20. Non-limiting exemplary retrieval devices are illustrated somewhat schematically in FIGS. 3-5.

Figure 3A:
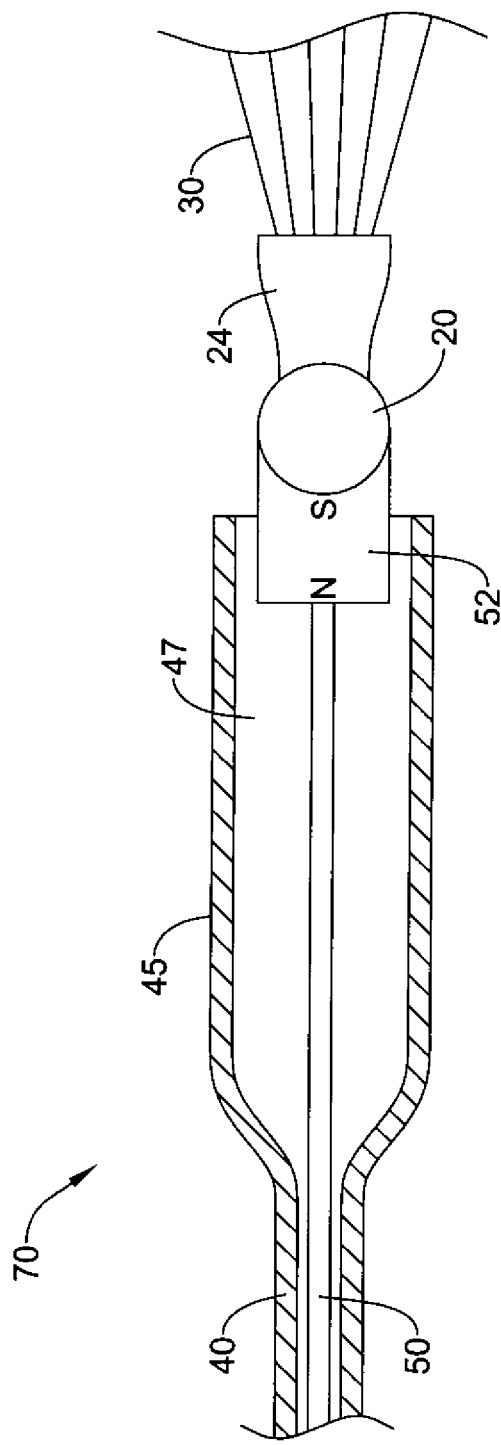
FIG. 3A illustrates a first retrieval device for a magnetically retrievable vena cava filter in a first position.
Figure 3B:
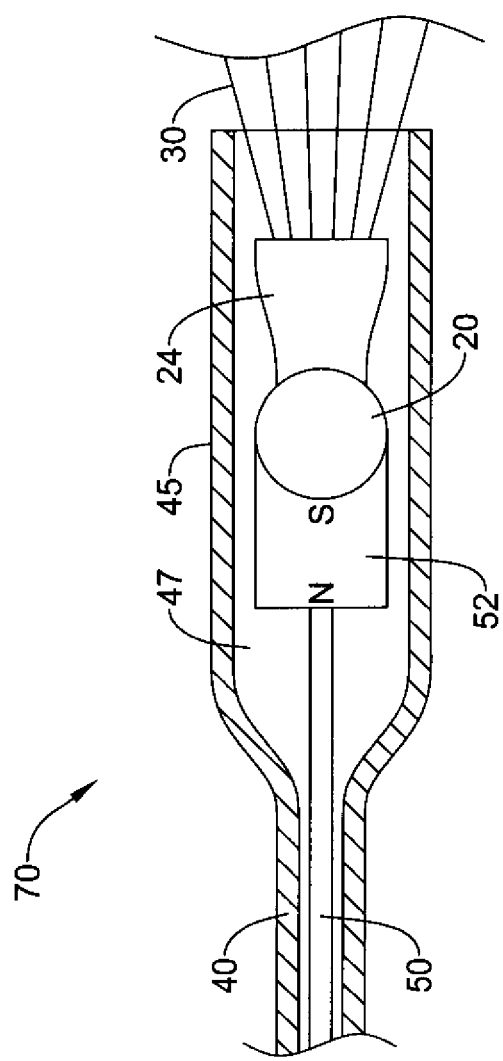
FIG. 3B illustrates a first retrieval device for a magnetically retrievable vena cava filter in a second position.

As illustrated in FIGS. 3A and 3B, retrieval device 70 comprises an elongate shaft 40 having fixedly attached to its distal end a housing 45 sized and adapted to receive substantially an entire magnetically retrievable vena cava filter 10 within a lumen 47 thereof. A magnetically active member 52 is actuatable within the lumen 47 of the housing 45 from a first position in which at least a portion of the magnetically active member 52 extends distally beyond the housing 45 and a second position in which the magnetically active member 52 is located near the proximal end of the housing 45. The magnetically active member 52 may be actuatable by any of the means known for that purpose such as the illustrated shaft 50, a tether, pneumatic or hydraulic actuators, and the like. When the magnetically active member 52 in the first position is advanced to the vicinity of the vena cava filter 10, magnetic attraction between the magnetically active member 52 and either the solid sphere 20 of magnetically permeable material of the embodiment of FIG. 1 or the spherical dipole magnet 126 of the embodiment of FIG. 2 will cause them to self-align thereby facilitating the retrieval of the associated vena cava filter 10.

In addition to self-alignment of magnetically active components of the vena cava filter 10 and the magnetically active member 52, their mutual attraction allows the vena cava filter 10 to be drawn proximally into the housing 45. In the alternative, the attractive force between magnetically active components of the vena cava filter 10 and the magnetically active member 52 may serve to maintain contact as the housing 45 is advanced over the collapsed legs 30 of the vena cava filter 10. In some embodiments, the attractive force alone will suffice to allow the vena cava filter 10 to be withdrawn and positioned for retrieval within the housing 45.

In other embodiments, the attractive force between magnetically active components of the vena cava filter 10 and the magnetically active member 52 may be supplemented by the addition of a retractable filter engaging member or latch 62, 162 adapted to engage the solid sphere 20 of magnetically permeable material; the apical head 24, 124; and/or the legs 30 of the vena cava filter 10. As in the case of the magnetically active member 52, it will be appreciated that a filter engaging member or latch, if present, may be actuatable and withdrawn by any of the means known for that purpose such as a shaft, a tether, pneumatic or hydraulic actuators, and the like. The engaging component or latch may include hooks, loops, tapers, barbs, detents, grasping elements, threaded connectors, and the like. In some embodiments, the filter engaging member is operably connected to an actuator located proximate the proximal end of the elongate shaft.

Figure 4:
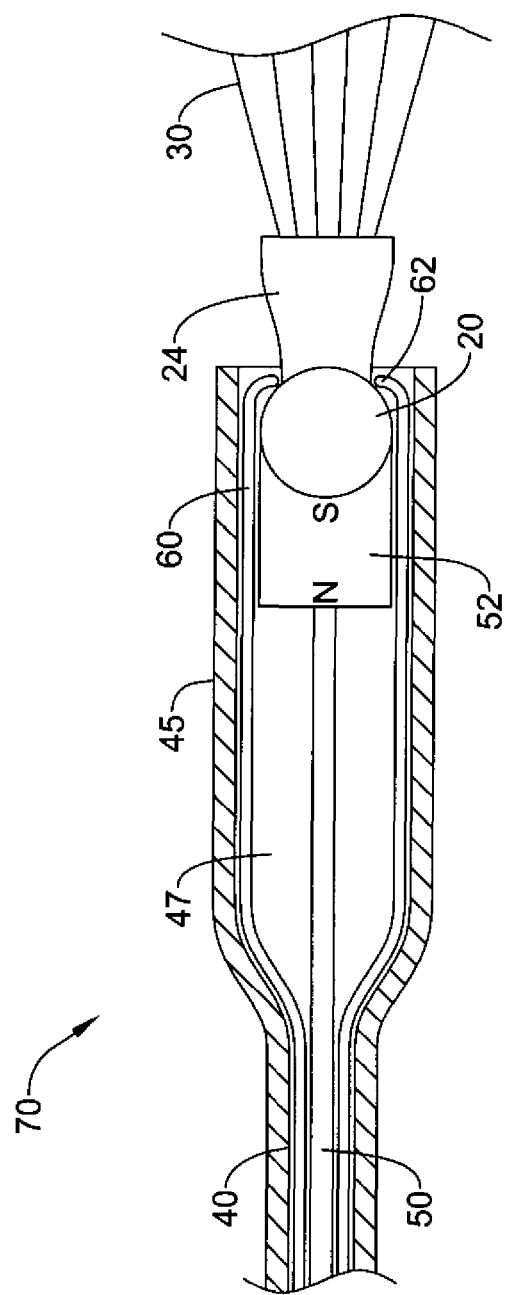
FIG. 4 illustrates another retrieval device for a magnetically retrievable vena cava filter.
Figure 4A:
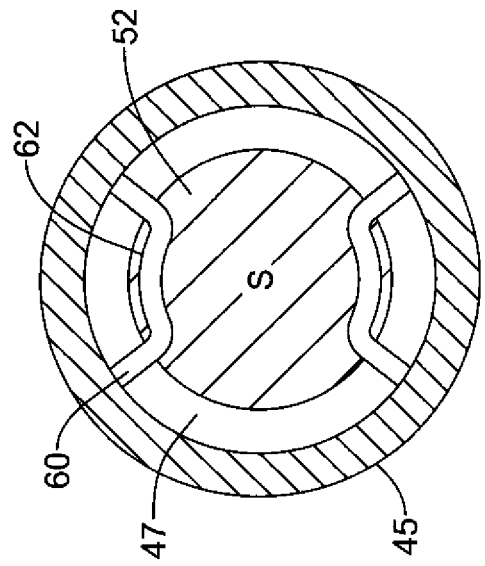
FIG. 4A illustrates an exemplary latch in a disengaged position.
Figure 4B:
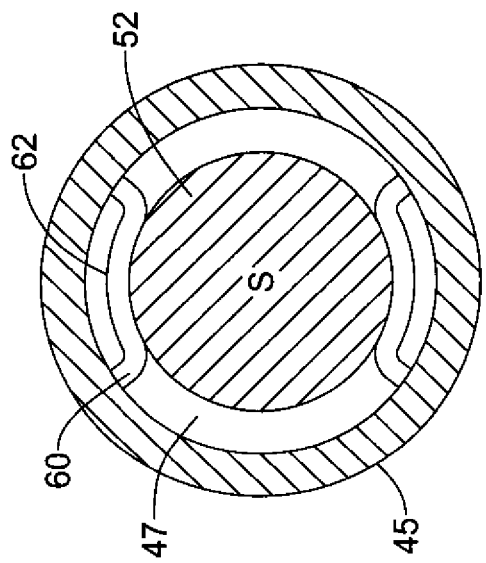
FIG. 4B illustrates an exemplary latch in an engaged position.

In the embodiment of FIGS. 4, 4A, and 4B, a latch 62 comprises two or more wires 60 having a first position generally along the wall of the housing 45 prior to magnetic engagement as illustrated in FIG. 4A. The latch 62 is biased toward the longitudinal axis of the housing 45 such that when the magnetically active member 52 and magnetically permeable sphere 20 and/or apical head 24, 124 are withdrawn proximally relative to the housing 45, the latch 62 mechanically engages the magnetically permeable sphere 20 and/or apical head 24, 124 as shown in FIG. 4B thereby allowing additional retraction force to be applied to the vena cava filter 10 by an associated actuating mechanism.

Figure 5A:
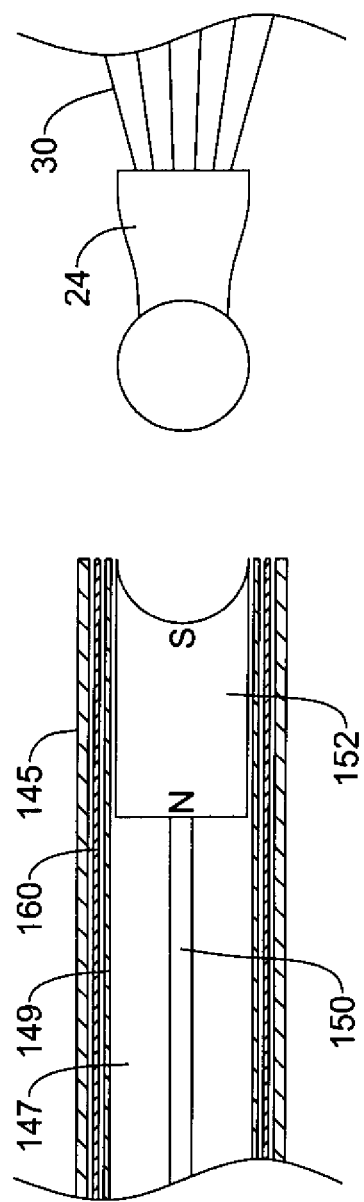
FIG. 5A illustrates another retrieval device for a magnetically retrievable vena cava filter in a disengaged position.
Figure 5B:
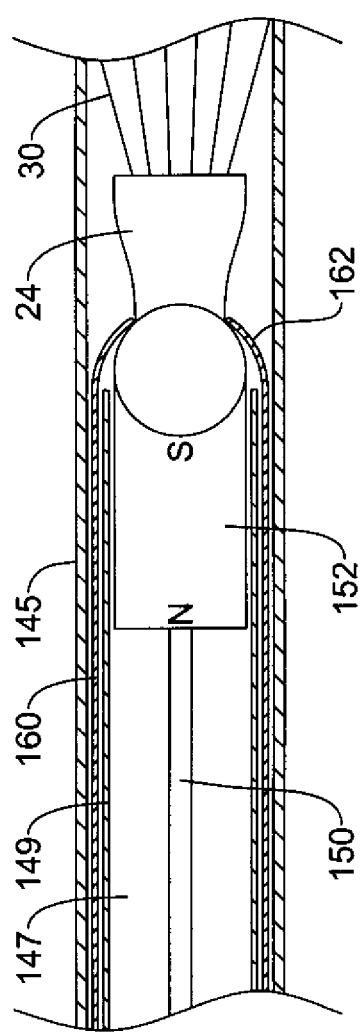
FIG. 5B illustrates another retrieval device for a magnetically retrievable vena cava filter in a disengaged position.

In the embodiment of FIGS. 5A and 5B, latch 162 is formed from a shape memory material 160, such as Nitinol (nickel-titanium), copper-zinc-aluminum-nickel, copper-aluminum-nickel, certain iron or cobalt-based alloys, certain polymers such as polyethylene oxide-polyethylene terephthalate, and the like, disposed between outer housing 145 and an inner tubular member 149. Following magnetic alignment and engagement between magnetically active member 152 and apical head 24 several modes of action are possible. The shape memory material 160 may be advanced from between outer housing 145 and an inner tubular member 149 to engage, the apical head 24, whereupon the outer housing 145 may be advanced to encase the vena cava filter 10 in preparation for removal of the filter. In the alternative, the magnetically active member 152, inner tubular member 149, and shape memory material latch 162 may be withdrawn together relative to stationary outer housing 145. Variations in details of the retrieval process are also possible as in the operation of the retrieval device of FIGS. 4, 4A, and 4B. In addition, the retrieval device may cooperate with additional elements, such as catheters and sheaths, which may provide optional elements of a deployment and/or retrieval system.

Although not illustrated herein, alternate latch configurations which engage one or more filter legs 30 concurrently with or following magnetic engagement between the vena cava filter 10 and a magnetically active member 52, 152, 252 are also contemplated.

Figure 6:
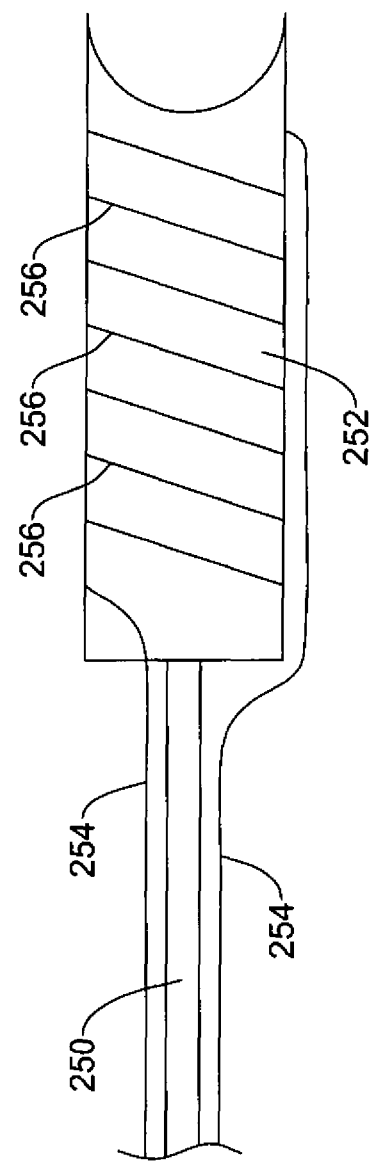
FIG. 6 illustrates an alternate magnetically active member.

As noted above, various combinations of mutually magnetically attractive elements may be employed in fabricating a vena cava filter 10 and retrieval device 70 for use as a retrieval system. In some embodiments, a magnetically permeable sphere 20 attached to the apical head 24 of the vena cava filter 10 may be used with a permanent magnet 52, 152 or with an electromagnetic active member 252 such as illustrated in FIG. 6 in which current supplied by wires 254 to coil 256 allows the electromagnet to be activated as desired. In other embodiments, a spherical dipole magnet 126 within the apical head 124 of the vena cava filter 10 may be used with a permanent magnet 52, 152, an electromagnetic active member 252, or a magnetically active member comprising magnetically permeable material.

Although the illustrative examples described above relate to vena cava filters and retrieval devices therefor, it is contemplated that the principles and structures described herein may also be applied to other filters and medical devices which may be implanted in a body lumen.

Various modifications and alterations of this invention will become apparent to those skilled in the art without departing from the scope and principles of this invention, and it should be understood that this invention is not to be unduly limited to the illustrative embodiments set forth hereinabove. It will be appreciated that the vena cava filters and/or the retrieval devices of this invention may include other elements, such as radiopaque marker bands, which may enhance the utility of the system. Other medical devices may incorporate the magnetically active components described in conjunction with the vena cava filter embodiment and retrieval device therefor. All publications and patents are herein incorporated by reference to the same extent as if each individual publication or patent was specifically and individually indicated to be incorporated by reference.

What is claimed is:

1. A magnetically retrievable vena cava filter having a low torque associated therewith when subjected to a strong magnetic field, said filter comprising:
   an apical hub defining therein a generally spherical cavity;
   a plurality of legs each having a first end fixedly attached to the apical hub and a second free end, said plurality of legs defining a generally conical filter basket in a deployed configuration; and
   a spherical dipole magnet located within the spherical cavity of the apical hub wherein the spherical dipole magnet is free to rotate about any axis passing through the center of the sphere.

2. The magnetically retrievable vena cava filter of claim 1, wherein each of the plurality of legs has a tissue anchor associated with its free end.

3. The magnetically retrievable vena cava filter of claim 1, wherein the spherical dipole magnet comprises neodymium-iron-boron.

4. The magnetically retrievable vena cava filter of claim 1, wherein the spherical dipole magnet comprises samarium-cobalt.

\* \* \* \* \*